US008105241B2

(12) United States Patent
Nelson et al.

(10) Patent No.: US 8,105,241 B2
(45) Date of Patent: Jan. 31, 2012

(54) COMBINING TO A SINGULARITY PLURAL-ANATOMICAL-SITE, HEART-FUNCTIONALITY MEASUREMENTS

(75) Inventors: Alex T. Nelson, Portland, OR (US); Patricia A. Arand, McMinnville, OR (US); Marco Dalla Gasperina, Vancouver, WA (US)

(73) Assignee: Inovise Medical, Inc., Beaverton, OR (US)

( * ) Notice: Subject to any disclaimer, the term of this patent is extended or adjusted under 35 U.S.C. 154(b) by 501 days.

(21) Appl. No.: 12/288,712

(22) Filed: Oct. 22, 2008

(65) Prior Publication Data

US 2009/0112107 A1 Apr. 30, 2009

Related U.S. Application Data

(60) Provisional application No. 61/000,615, filed on Oct. 26, 2007.

(51) Int. Cl.
*A61B 5/04* (2006.01)
(52) U.S. Cl. ........................................................ 600/508
(58) Field of Classification Search .................. 600/508, 600/528
See application file for complete search history.

(56) References Cited

U.S. PATENT DOCUMENTS

| | | | |
|---|---|---|---|
| 5,392,780 A | 2/1995 | Ogino et al. | |
| 7,039,538 B2 * | 5/2006 | Baker, Jr. ........................ | 702/78 |
| 7,174,203 B2 | 2/2007 | Arand et al. | |
| 7,225,021 B1 | 5/2007 | Park et al. | |
| 7,559,903 B2 | 7/2009 | Moussavi et al. | |
| 2003/0187337 A1 | 10/2003 | Tarassenko et al. | |
| 2004/0127792 A1 | 7/2004 | Siejko et al. | |
| 2005/0027323 A1 | 2/2005 | Mulligan et al. | |
| 2008/0021510 A1 | 1/2008 | Mi et al. | |
| 2008/0177191 A1 | 7/2008 | Patangay et al. | |
| 2009/0165559 A1 | 7/2009 | Lec | |

OTHER PUBLICATIONS

International Search Report, U.S. Appl. No. PCT/US10/055696, dated Dec. 23, 2010, 13 pages total.
USPTO Office Action, U.S. Appl. No. 12/315,165, dated Nov. 12, 2010, 9 pages total.
USPTO Office Action, U.S. Appl. No. 11/264,328, dated May 9, 2008, 7 pages total.
USPTO Office Action, U.S. Appl. No. 11/264,328, dated Oct. 16, 2008, 8 pages total.
USPTO Office Action for U.S. Appl. No. 12/321,646 dated Jun. 17, 2011. 9pp.
USPTO Office Action for U.S. Appl. No. 12/321,650 dated Sep. 7, 2011. 8pp.
USPTO Office Action for U.S. Appl. No. 12/321,647 dated Jun. 1, 2011. 7pp.

* cited by examiner

*Primary Examiner* — Eric D. Bertram
(74) *Attorney, Agent, or Firm* — Jon M. Dickinson, P.C.; Robert D. Varitz, P.C.

(57) ABSTRACT

Combining, to a singularity, from a plurality of anatomical sites, and over a plurality of heart cycles a collection of selected heart-functionality parameter measurements, such as EMAT, LVST, PADT, and AAFT measurements, including (a) collecting ECG and heart-sound data from plural anatomical sites, (b) computer processing such data to acquire plural, per-site, per-heart-cycle, nominal values for the selected parameter, (c) utilizing arithmetic mean and selected variance calculations related to such nominal values processing, and determined weight coefficients, computing weighted nominal values, (d) computing a weighted, nominal-value average of all of the nominal values by summing all of the weighted values and dividing that sum by the sum of all of the weight coefficients, and (e) presenting the computed weighted average as the combined, singularity value of the selected heart-functionality parameter.

2 Claims, 1 Drawing Sheet

COMBINING TO A SINGULARITY PLURAL-ANATOMICAL-SITE, HEART-FUNCTIONALITY MEASUREMENTS

CROSS REFERENCE OF RELATED APPLICATION

This application claims priority to the filing date, Oct. 26, 2007, of U.S. Provisional Patent Application Ser. No. 61/000,615, covering an invention entitled "Q-Onset Ventricular Depolarization Detection in the Presence of a Pacemaker". The entire disclosure content of that prior-filed provisional application is hereby incorporated herein by reference.

BACKGROUND AND SUMMARY OF THE INVENTION

This invention relates to an electroacoustic, cardiographic method for combining, to a singularity from a plurality of anatomical source sites, various heart-functionality parameter measurements.

In the context of electroacoustic cardiography it is generally desirable to produce measurements from more than one anatomical site, thus to provide an important measure of signal-gathering robustness relative to noise, and also to furnish good assurance that the resulting information will not depend too much on the particular conditions of signal gathering existing at but a single anatomical site. However, in order successfully to produce a single set of measurements to a clinician, measurements from such multiple anatomical sites must in some fashion be appropriately combined.

Accordingly, the present invention focuses attention on a unique method for combining such parameter measurements derived from multiple, captured events at more than one anatomical site.

In the context of electroacoustic cardiography, examples of plural-anatomical-site, event-wise measurements include, as just an illustration, the sequence of electromechanical activation times—EMAT—as measured during each cardiac cycle during which data is collected. Collected data to yield such a measurement includes, of course, both ECG information and heart-sound information. If appropriate electrical and acoustic sensors are located, for example, at two anatomical sites, then two separate sequences of EMAT measurements would be available, and such two measurements squarely present the issue of achieving an appropriate combination of these measurements so that a clinician will be working with useful EMAT measurement data as a singularity.

In terms of the practice of the present invention, other important heart-functionality parameters, in addition to the EMAT parameter, include LVST, PADT, and AAFT. Also in terms of the practice of the invention, and as will become apparent, the number of plural sites which can be handled is not limited to just two sites.

According to a preferred and best-mode manner of practicing the invention, a practice which involves uniquely algorithmically programmed, digital-computer data-processing, the steps of the invention may be expressed in the following sequence: (a) over a predetermined number of cardiac cycles, collecting ECG and heart-sound data, including plural-anatomical-site heart-sound data, relevant to the measurement of a selected, heart-functionality parameter, (b) computer processing such collected data to acquire per-site, per-cycle nominal measurement values for that parameter (such as for any one of the four, above-identified parameters; (c) relative to each anatomical site, computing the arithmetic mean of the nominal selected-parameter measurement values associated with that site by summing all of such site-associated nominal values and dividing that sum by the predetermined number of cycles; (d) also relative to each site, computing the variance of the associated nominal values by summing the squared difference between each such nominal value and the computed arithmetic mean, and dividing this squared-difference sum by the predetermined number of cycles; (e) computing weighted values for all of the nominal values that are associated with all of the plural anatomical sites by multiplying each such per-site value by a weight coefficient which is equal to the inverse of the variance that is associated with the value's associated anatomical site; (f) computing the weighted average of all of the nominal values that are associated with all of the plural anatomical sites by summing all of the weighted values and then dividing that weighted-value sum by the sum of all of the weight coefficients; and (g) presenting the computed weighted average as being the assessed, combined, singular value of the selected parameter.

These and other features and advantages which are offered by the present invention will become more fully apparent as the detailed description of the invention which shortly follows is read in conjunction with the accompanying single drawing FIGURE.

DETAILED DESCRIPTION OF THE INVENTION

Figure 1:
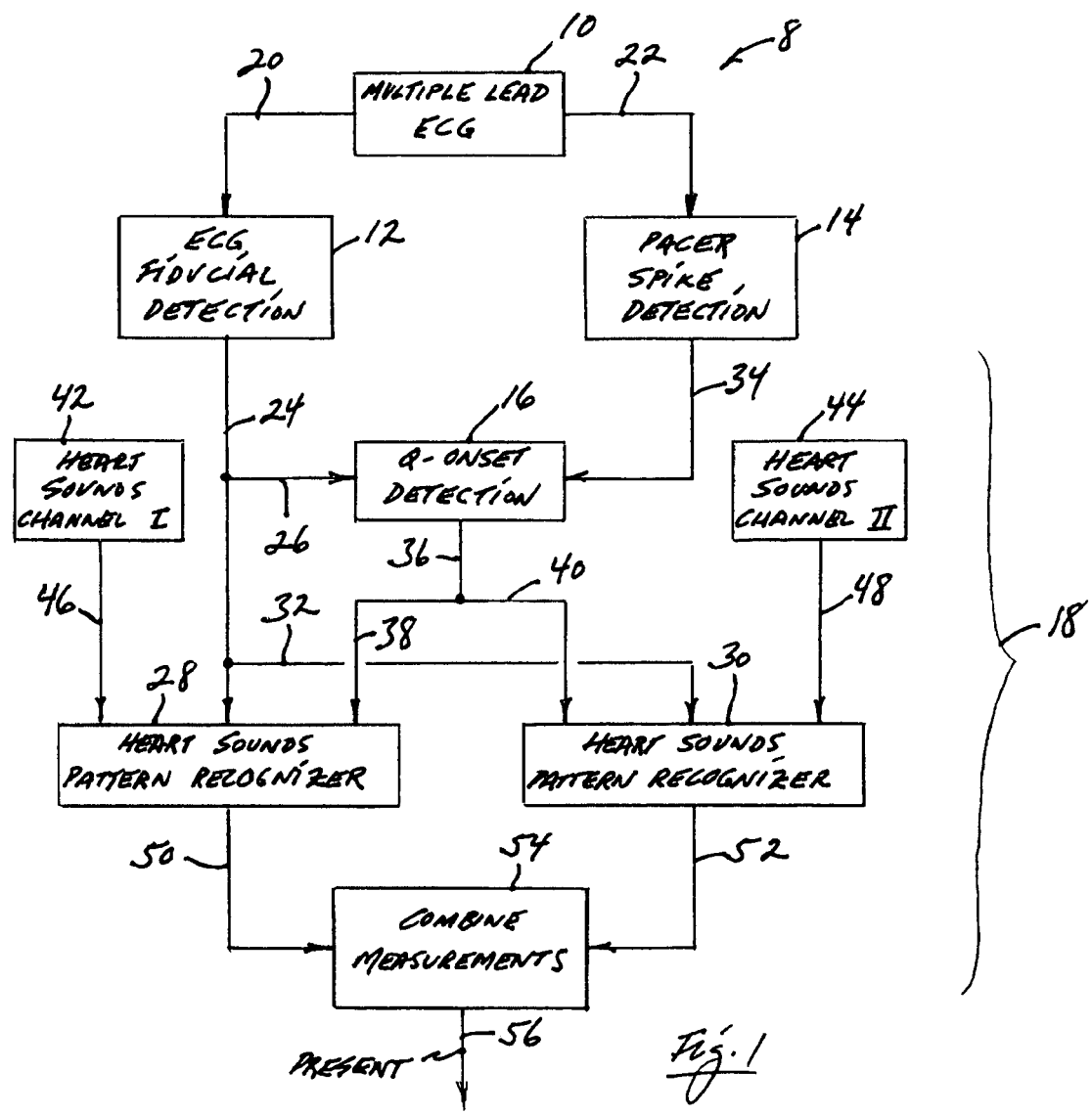
FIG. 1, the single drawing FIGURE, presents a block/schematic diagram illustrating both the structural architecture and the methodology of the preferred and best-mode manner of practicing the present invention.

Turning attention to this single drawing FIGURE, indicated, among other things, generally at 8 in block/schematic form are a system and a methodology which employ the structural architecture and the unique methodology of a preferred and best-mode form of the present invention. For the purpose of illustration herein, the structure and methodology of the invention are pictured in this FIGURE in a condition organized to deal with a relatively common situation wherein it is required that there be an accommodation to deal with the presence of an operating pacemaker with respect to a subject—a patient—wherein plural-anatomical-site heart-functionality parameters are to be measured.

While this pictured situation involving the presence of an active pacemaker has been chosen, as just mentioned, for illustration purposes, it should be understood that practice of the invention does not at all require the presence of a pacemaker, or pacer, and can of course operate, without modification, in a situation where no pacemaker is involved. The involvement of a pacemaker, naturally, poses the issue of determining where one key fiducial event, the Q-onset fiducial, precisely occurs. This involvement can cloud the issue of determining the correct start timing of the Q-onset fiducial with accuracy because of the fact that effective Q-onset may, in any given heart cycle, or heartbeat, be marked either by (a) intrinsic, anatomical Q-onset behavior, or (b) via the action of a pacer pulse (or spike). Obviously, in order that many parameter measurements may be made accurately, it is always important that such a fiducial be accurately determined so that there is a high degree of reliability with respect measurements that are made which depend upon knowledge of the time location within a heartbeat of Q-onset.

Accordingly, included in the structural and methodologic arrangement pictured in FIG. 1 are four blocks 10, 12, 14, 16 which variously play several roles in the practice of the invention, including a role played collectively relating to the presence of an operating pacemaker, to provide accurate Q-onset detection—a specific task which, ultimately, is performed by an appropriately algorithmically programmed, associated digital computer which is represented in FIG. 1 by the lateral bracket shown at 18.

Block 10 represents conventional collection of multiple-lead (such as 12-lead) ECG information, which information is sent, via data connections 20, 22 to blocks 12, 14, respectively. Block 12 examines the ECG information conventionally to provide preliminary fiducial detection, sending initially detected Q-onset and QRS-wave data to block 16 via data connections 24, 26, and P-onset and R-peak-value data to two additional blocks 28, 30 via data connections 24, 32, respectively. Block 14 functions in any suitable manner, which may be entirely conventional in nature, to identify pacer spike timing information and spike classification information which is supplied over a data connection 34 to block 16 wherein precision Q-onset detection takes place as will shortly be described. Block 16, under the control of previously mentioned, algorithmically programmed computer 18, calculates and sends accurately determined, per-cardiac-cycle, Q-onset fiducial timing information via data connections 36, 38 to block 28, and via data connections 36, 40 to block 30.

While, in relation to the operation of block 16, there are, indeed, many ways in which the timing of the Q-onset fiducial may be determined and utilized in the practice of the present invention, we now provide herein a general description of one interesting way in which such accurate Q-onset determination may be accomplished under circumstances where, as is true in the present illustration of the invention, an active pacemaker is involved. This description essentially constitutes an algorithm programmed, and operational, within computer 18.

This algorithm for Q-onset determination, per cardiac cycle, is expressible in the following terms which will be clearly understandable by those skilled in the relevant art:

(1) during a predetermined time span, such as about 10-seconds, which includes a plurality of successive, QRS cardiac cycles, gathering both ECG and pacemaker-spike information for, and within, each such cycle;

(2) with respect to each such gathered cardiac cycle, time-locating, identifying and time-position sorting, first to last, each intrinsic Q-onset and each pacemaker-spike event, including specifically identifying each pacemaker-spike event as being one of ventricular or bi-ventricular;

(3) also with regard to each such cardiac cycle, evaluating, with respect a single, selected, QRS waveform, such as the V4 waveform, the waveform slope therein from (a) a time just preceding, to (b) a time just following, the mentioned, time-position sorted, first-in-time and last-in-time one of such time-located, identified and sorted events, respectively;

(4) from the mentioned slope evaluating practice, finding the time, in the mentioned, single, selected QRS-waveform, of the first substantial QRS-waveform slope change; and (5) in each cardiac cycle, selecting to be the correct Q-onset therein the time-sorted event in that cycle whose time position most immediately precedes the time of the mentioned, found, first-substantial slope change.

Continuing now with a description of the methodology of the invention, and its architecture, as such are illustrated in the single drawing FIGURE, and recalling that this invention is focused upon combining, to a singularity, heart-functionality parameters which have been calculated and which are based upon data derived from two or more anatomical sites, indicated generally at 40, 42 are blocks which are marked, respectively, "Heart Sounds Channel I", and "Heart Sounds Channel II". Each of blocks 42, 44 represents conventional collection, from two, different, selected, anatomical sites with respect to a particular patient, of heart-sound information (S1, S2, S3, and S4). This gathered, heart-sound acoustic information is delivered via data connections 46, 48 from blocks 42, 44, respectively, to previously mentioned blocks 28, 30, respectively, which, as indicated in the drawing FIGURE, function as heart sounds pattern recognizers.

Thus it is the case that the two heart sounds pattern recognizer blocks 28, 30 receive certain ECG fiducial information, including Q-onset, P-onset, and R-peak-value, as well as information from blocks 42, 44 respecting the S1, S2, S3, and S4 heart sounds derived from the two, illustrative and mentioned anatomical sites. Under the control of computer 18, conventional computations are performed within the realms of blocks 28, 30 to determine one (or more) selected, heart-functionality parameter(s), such as the EMAT, LVST, PADT, and AAFT parameters.

Following computations in blocks 28, 30, over a selected plurality of data-gathering cardiac cycles, of the per-site, plural-cycle nominal values of a common, or the same, heart-functionality parameter, such as the EMAT parameter, the two sets of, calculated parameter values, referred to herein as the nominal parameter values, are supplied by blocks 28, 30 via data connections 50, 52, respectively, to a "Combine Measurements" block 54. Within block 54, under the control of algorithmically programmed computer 18, the thus-furnished nominal parameter values are utilized to create, as a singularity, a combined EMAT parameter value in accordance with the following, unique "combining" algorithm proposed in accordance with a key feature of the present invention:

(1) Relative to each, involved anatomical site, computing the arithmetic mean of the plural-cycle-relevant, nominal, selected-parameter values associated with that site by summing all of such site-associated nominal values, and dividing the sum by the predetermined number of cycles of data collection;

(2) Also relative to each site, computing the variance of the associated nominal values by summing the squared difference between each such nominal value and the computed arithmetic mean, and dividing this squared-difference sum by the predetermined number of cycles;

(3) Computing weighted values for all of the nominal values that are associated with all of the plural anatomical sites by multiplying each such per-site value by a weight coefficient which is equal to the inverse of the variance that is associated with the value's associated anatomical site;

(4) Computing the weighted average of all of the nominal values that are associated with all of the plural anatomical sites by summing all of the weighted values and then dividing that weighted-value sum by the sum of all of the weight coefficients; and (5) Presenting the computed weighted average as being the assessed, combined, singular value of the selected heart-functionality parameter.

From, and following, the implementation of this unique algorithm, block 54 furnishes, or presents, over an appropriate output which is represented by arrow-headed line 56, a computed, weighted average which is deemed to be the assessed, combined, desired, singular value of a particular, selected heart-functionality parameter, such as the EMAT parameter.

Thus, the present invention provides a unique and highly satisfactory manner of combining, into a singularity, pre-calculated heart-parameter values which have been derived from data acquired from a plurality of a patient's, or a subject's, anatomical sites. As has been mentioned earlier, the number of sites associated with this plurality may be two or more, with the algorithm which is performed in block 54 being fully capable, under the control of an appropriately algorithmically program digital computer, such as computer 18, of handling and combining all such measurement values.

Overall, the methodology of the invention, in very general terms, can be expressed as being an electroacoustic, cardiographic, computer-implemented method for combining, to a singularity from a plurality of anatomical source sites, heart-functionality parameter measurements including (a) over a predetermined number of cardiac cycles, collecting ECG and heart-sound data, including plural-anatomical-site heart-sound data, (b) computer processing such collected data to acquire per-site, per-cycle nominal values for the selected parameter, (c) relative to each site, computing the arithmetic mean of the nominal selected-parameter values associated with that site by summing all of such site-associated nominal values and dividing the sum by the predetermined number of cycles, (d) also relative to each site, computing the variance of the associated nominal values by summing the squared difference between each such nominal value and the computed arithmetic mean, and dividing this squared-difference sum by the predetermined number of cycles, (e) computing weighted values for all of the nominal values that are associated with all of the plural anatomical sites by multiplying each such per-site value by a weight coefficient which is equal to the inverse of the variance that is associated with the value's associated anatomical site, (f) computing the weighted average of all of the nominal values that are associated with all of the plural anatomical sites by summing all of the weighted values and then dividing that weighted-value sum by the sum of all of the weight coefficients, and (g) presenting the computed weighted average as being the assessed, combined, singular value of the selected heart-functionality parameter.

In a more specific sense, the methodology of the invention may further be expressed, in the context just stated above, as involving, especially, the several heart-functionality parameters known as EMAT, LVST, PADT, and AAFT.

Accordingly, while a preferred and best-mode manner of implementing and practicing the present invention has been described herein and illustrated in detail, we appreciate that variations and modifications may be made without departing from the spirit of the invention.

We claim:

1. An electroacoustic, cardiographic, computer-implemented method for combining, to a singularity from a plurality of anatomical source sites, heart-functionality parameter measurements comprising over a predetermined number of cardiac cycles, collecting ECG and heart-sound data, including plural-anatomical-site heart-sound data, computer processing such collected data to acquire per-site, per-cycle nominal values for the selected parameter, relative to each site, computing the arithmetic mean of the nominal selected-parameter values associated with that site by summing all of such site-associated nominal values and dividing the sum by the predetermined number of cycles, also relative to each site, computing the variance of the associated nominal values by summing the squared difference between each such nominal value and the computed arithmetic mean, and dividing this squared-difference sum by the predetermined number of cycles, computing weighted values for all of the nominal values that are associated with all of the plural anatomical sites by multiplying each such per-site value by a weight coefficient which is equal to the inverse of the variance that is associated with the value's associated anatomical site, computing the weighted average of all of the nominal values that are associated with all of the plural anatomical sites by summing all of the weighted values and then dividing that weighted-value sum by the sum of all of the weight coefficients, and presenting the computed weighted average as being the assessed, combined, singular value of the selected heart-functionality parameter.

2. The method of claim 1, wherein the selected heart-functionality parameter is at least one of EMAT (electromechanical activation times), LVST (left ventricular systolic time), PADT (pre-atrial diastolic filling time), and AAFT (accelerated atrial filling time).

* * * * *